US010004626B1

(12) United States Patent
Stine

(10) Patent No.: US 10,004,626 B1
(45) Date of Patent: Jun. 26, 2018

(54) NECK MOVEMENT SUPPORT DEVICE, SYSTEM AND METHODS

(71) Applicant: Joseph P. Stine, Orlando, FL (US)

(72) Inventor: Joseph P. Stine, Orlando, FL (US)

(*) Notice: Subject to any disclaimer, the term of this patent is extended or adjusted under 35 U.S.C. 154(b) by 1052 days.

(21) Appl. No.: 14/211,418

(22) Filed: Mar. 14, 2014

Related U.S. Application Data

(60) Provisional application No. 61/781,194, filed on Mar. 14, 2013.

(51) Int. Cl.
A61H 1/02 (2006.01)
A61F 5/01 (2006.01)

(52) U.S. Cl.
CPC .......... A61F 5/0102 (2013.01); A61H 1/0292 (2013.01); A61H 1/0296 (2013.01)

(58) Field of Classification Search
CPC .......... A61H 1/00; A61H 1/02; A61H 1/0207; A61H 1/0218; A61H 1/0222; A61H 1/0292; A61H 1/0296; A61H 2001/0203; A61H 2201/0134; A61H 2201/0138; A61H 2201/0142; A61H 2201/0146; A61H 2201/0149; A61H 2201/1253; A61H 2201/1604; A61H 2201/1607; A61H 2201/1609; A61H 2201/1611; A61H 2205/04; A61F 5/04; A61F 5/042; A61F 5/05; A61F 5/055; A61F 5/05883; A63B 23/025; A63B 2023/006; A61G 13/009; A61G 13/121
USPC ................ 606/237, 240, 241, 242, 244, 245
See application file for complete search history.

(56) References Cited

U.S. PATENT DOCUMENTS

| | | | |
|---|---|---|---|
| 1,233,496 A * | 7/1917 | Nlchols | A61H 1/0222 606/242 |
| 2,791,999 A | 5/1957 | Bustamante | |
| 2,819,132 A * | 1/1958 | Rock | A61G 13/009 606/242 |
| 3,238,936 A * | 3/1966 | Siedentop | A61F 7/007 5/284 |
| 4,278,249 A | 7/1981 | Forrest | |
| 4,373,222 A * | 2/1983 | Wolfe | A47C 15/008 128/845 |
| 4,655,450 A | 4/1987 | Rogers, Jr. et al. | |
| 4,660,549 A | 4/1987 | Kowalski et al. | |
| 4,768,779 A | 9/1988 | Oehman, Jr. et al. | |
| 4,850,343 A * | 7/1989 | Scott | A61G 13/009 606/238 |
| 5,116,359 A * | 5/1992 | Moore | A61H 1/008 482/10 |

(Continued)

Primary Examiner — Michael Tsai
(74) Attorney, Agent, or Firm — Allen Dyer Doppelt & Gilchrist PA

(57) ABSTRACT

A neck movement support device includes a stationary member, a movable member connected to the stationary member and rotatable relative thereto about an anteroposterior neck movement axis, a yoke extending away from the movable member and rotatable therewith about the anteroposterior neck movement axis, a handle connected to the yoke and rotatable relative thereto about a mediolateral neck movement axis, and a head hardness connected to the handle and rotatable relative thereto about a craniocaudal neck movement axis. A head of a user is securable to the head hardness, so as to constrain the head to move or remain stationary along with the head hardness about the anteroposterior, mediolateral and craniocaudal neck movement axes.

32 Claims, 6 Drawing Sheets

(56) References Cited

U.S. PATENT DOCUMENTS

| | | | |
|---|---|---|---|
| 5,192,306 A * | 3/1993 | Scott | A61G 13/009 |
| | | | 5/608 |
| 5,336,138 A | 8/1994 | Arjawat | |
| 5,569,175 A * | 10/1996 | Chitwood | A61F 5/04 |
| | | | 128/845 |
| 6,213,558 B1 * | 4/2001 | Axelson | A47C 7/425 |
| | | | 297/464 |
| 6,436,126 B1 | 8/2002 | McAfee | |
| 6,599,257 B2 | 7/2003 | Al-Obaidi et al. | |
| 6,638,299 B2 * | 10/2003 | Cox | A61H 1/0222 |
| | | | 5/617 |
| 7,189,214 B1 * | 3/2007 | Saunders | A61F 5/04 |
| | | | 5/618 |
| 7,601,132 B2 | 10/2009 | Nichols et al. | |
| 8,485,195 B2 | 7/2013 | River et al. | |
| 8,529,480 B2 | 9/2013 | Dicerbo et al. | |
| 2002/0170115 A1 * | 11/2002 | Borders | A61G 12/00 |
| | | | 5/600 |
| 2009/0204039 A1 * | 8/2009 | Elan | A61H 1/0296 |
| | | | 602/18 |
| 2009/0272385 A1 * | 11/2009 | River | A61H 1/0296 |
| | | | 128/845 |
| 2013/0019877 A1 | 1/2013 | Sklar | |

* cited by examiner

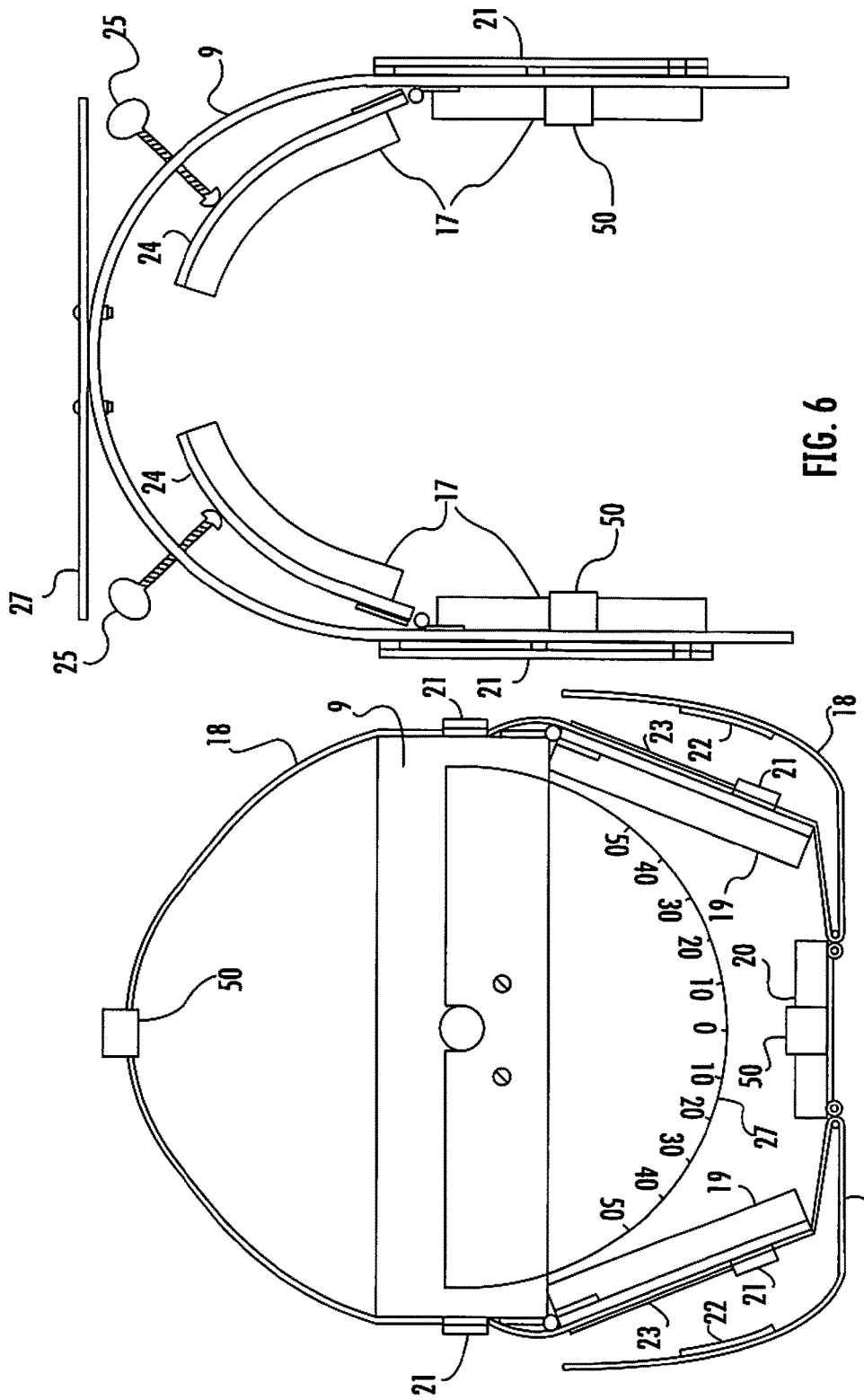

NECK MOVEMENT SUPPORT DEVICE, SYSTEM AND METHODS

CROSS-REFERENCE TO RELATED APPLICATION

This application claims the benefit of U.S. Provisional Patent Application Ser. No. 61/781,194, filed on Mar. 14, 2013, the contents of which are herein incorporated by reference in their entirety.

FIELD OF THE INVENTION

The present invention relates to neck movement support devices, and more particularly to devices for therapeutic diagnosis and treatment of the joints of the neck and related muscles.

BACKGROUND OF THE INVENTION

The term "proprioceptive neuromuscular facilitation" ("PNF") refers to stretching techniques used in a clinical environment to enhance a patient's both active and passive ranges of motion. Generally, an active PNF stretch involves a shortening contraction of the opposing muscle to place the target muscle on stretch, followed by an isometric contraction of the target muscle.

In the past, PNF treatment involved a therapist using his or her hands to stretch the muscle group of a joint to the end of its current range of motion. Then the patient contracts the muscle group isometrically in the stretched position against resistance from the therapist's hands for a brief period of time. The muscle group is then allowed to relax briefly before being stretched again by the therapist to an increased range of motion when the muscles are again contracted isometrically in the stretched position against resistance by the therapist. This routine is continued until no further range of motion is achieved or the patient becomes fatigued.

In the case of PNF neck therapy, the patient lies on a table with the head extending beyond one end of the table, while the therapist holds the sides of the head and moves the head to a desired position to stretch the target muscle group. Progress is determined by the improved angle of motion of the neck from its normal position. The angle is either estimated or measured using a protractor. Because both hands of the therapist are required during the stretch and hold, a protractor is difficult to use, resulting in inaccurate measurement. The therapist may have a difficult time holding the head in a fixed position against the force applied by the patient's head. Also, the force needed to hold the patient's head is fatiguing for the therapist.

SUMMARY OF THE INVENTION

In view of the foregoing, it is an object of the present invention to provide an improved neck movement support device, and related systems and methods. According to an embodiment of the present invention, a neck movement support device includes a stationary member, a movable member connected to the stationary member and rotatable relative thereto about an anteroposterior neck movement axis, a yoke extending away from the movable member and rotatable therewith about the anteroposterior neck movement axis, a handle connected to the yoke and rotatable relative thereto about a mediolateral neck movement axis, and a head harness connected to the handle and rotatable relative thereto about a craniocaudal neck movement axis. A head of a user is securable to the head harness, so as to constrain the head to move or remain stationary along with the head harness about the anteroposterior, mediolateral and craniocaudal neck movement axes.

An aspect of the present invention is more particularly directed to a system and method for achieving PNF stretching of the neck in one plane of motion while other planes of motion are held in a mechanically locked position, until such time as the therapist releases the associated locking mechanism. To this end, the system is provided with a harness for holding the patient's head adjacent and over one end of a therapy table, with the harness fitted to a yoke support that in turn is rotatable by a handle manipulated by the therapist from side to side. The harness within the yoke support can also be rotatable about other axes to achieve complete manipulation of the head. Means are provided for measuring the angular displacement of the patient's head relative to a reference. A hydraulic cylinder arrangement is attached between the end of the table and the yoke in order to lock the patient's head in a desired position so that the PNF stretching activities can proceed. The system includes restrictive means to insure that, while the patient is free to exercise the neck in one plane of motion, other planes of motion are held in a locked position.

Advantageously, the PNF system is under the control of the therapist, with the therapist's hands being replaced with the head harness. The therapist moves the system to a desired location and locks the head into that initial stretched position. When the patient applies force against the head harness, the resistance to that force is supplied by the head harness replacing the therapist's hands. The procedure of stretching, followed by isometric force from the patient and then relaxation is the same as explained above. Range of motion can be accurately measured by the system. After the PNF therapy is completed and improved range of motion is achieved, the stops in one plane of motion can be freed and the patient can actively exercise the joint though the improved range of motion.

These and other objects, aspects and advantages of the present invention will be better appreciated in view of the drawings and following detailed description of preferred embodiments.

BRIEF DESCRIPTION OF THE DRAWINGS

FIG. 6 is a front elevation view of the head harness frame of FIG. 4;

FIG. 7 is a top view of the head harness of FIG. 4; and

DETAILED DESCRIPTION OF PREFERRED EMBODIMENTS

Figure 1:
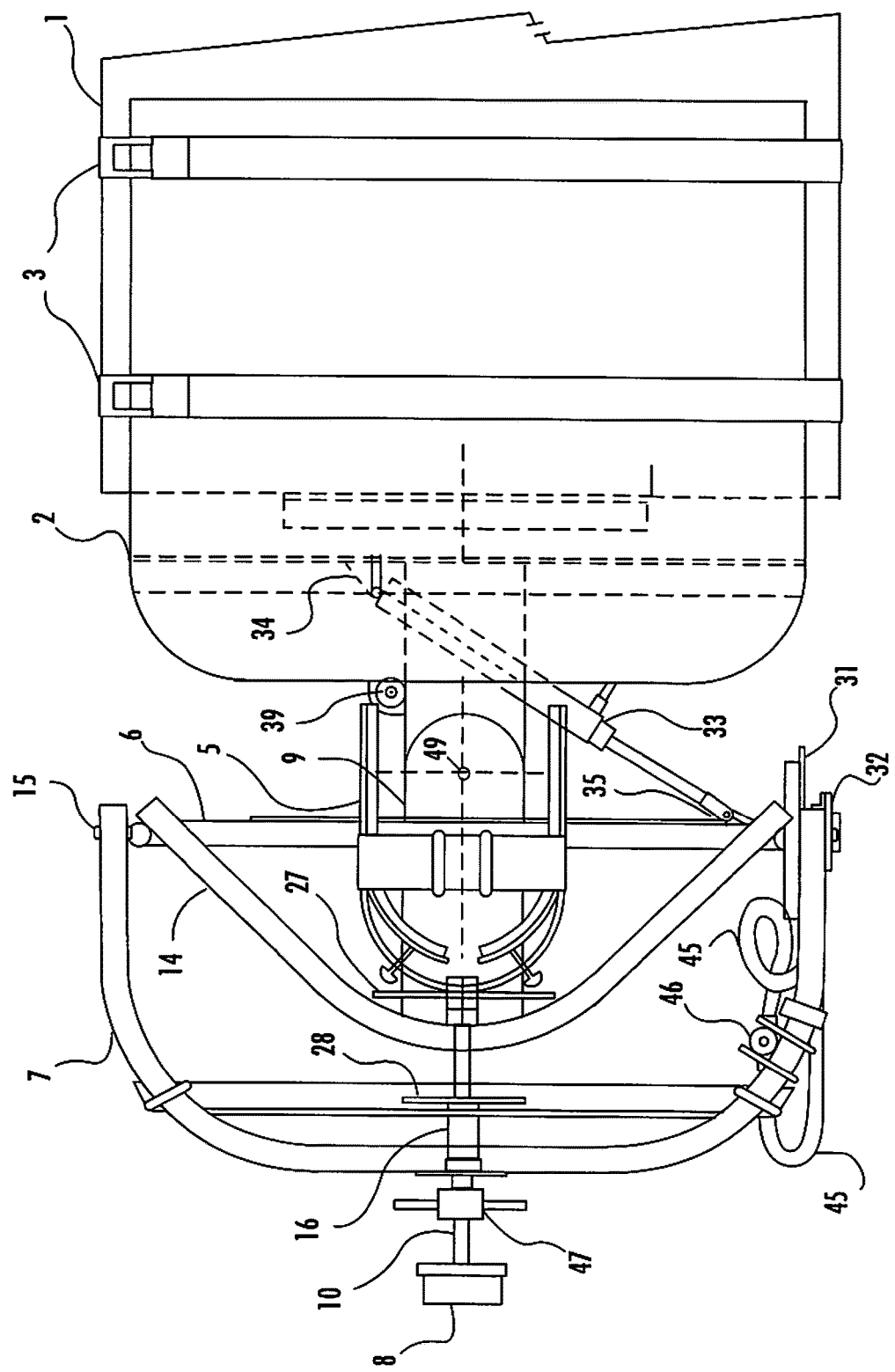
FIG. 1 is a plan view of a neck movement support device, according to an embodiment of the present invention.

The PNF stretching system and methods of this invention will now be described more fully with reference to the drawings in which a preferred embodiment of the invention for use in carrying out PNF stretching of the neck is shown and described. It will of course be understood by those skilled in the art that the invention may be embodied in different forms and should not be construed as limited to the illustrated embodiment described below and shown in the drawings.

Figure 2:
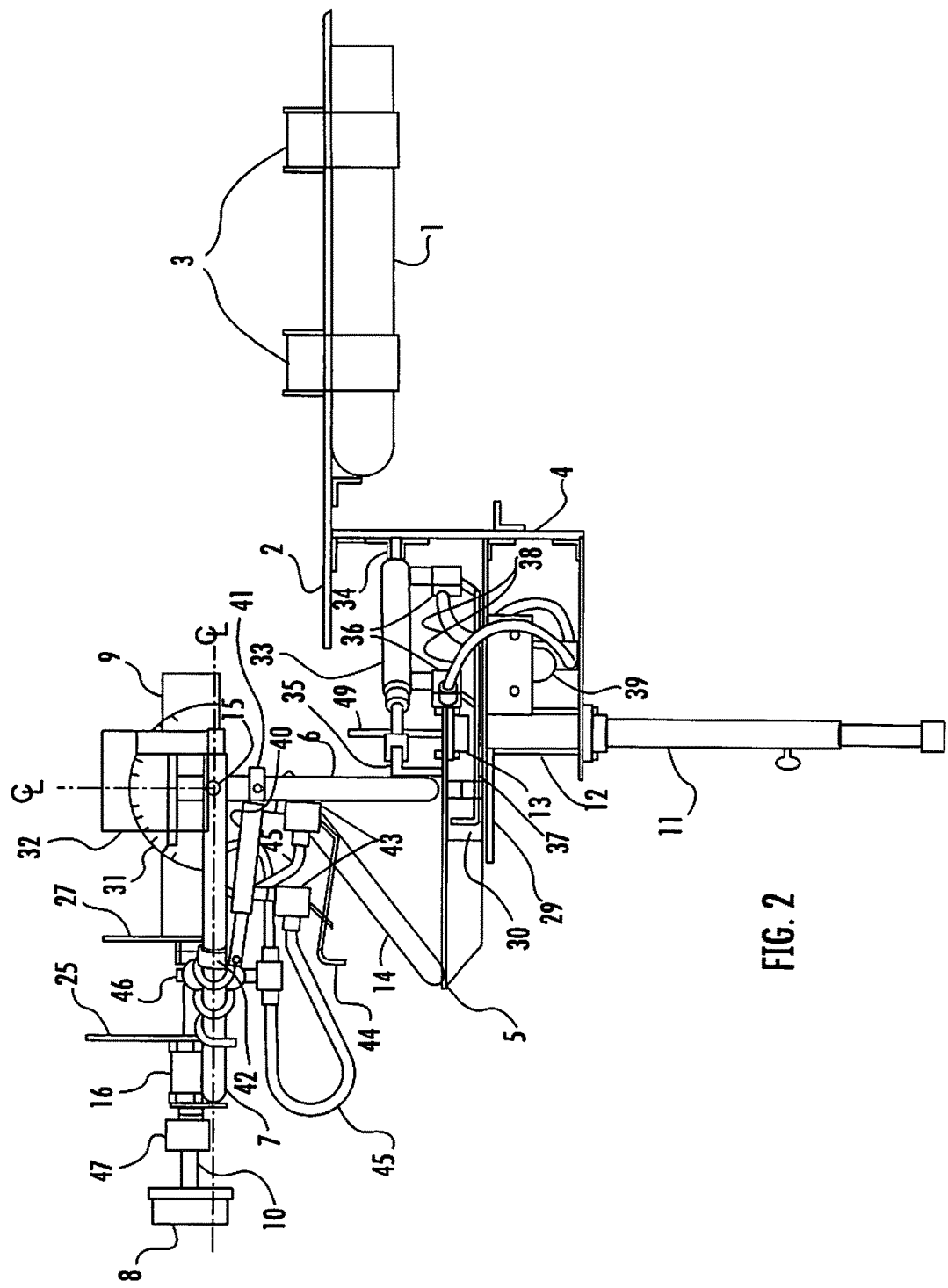
FIG. 2 is a right side elevation view of the device of FIG. 1.
Figure 3:
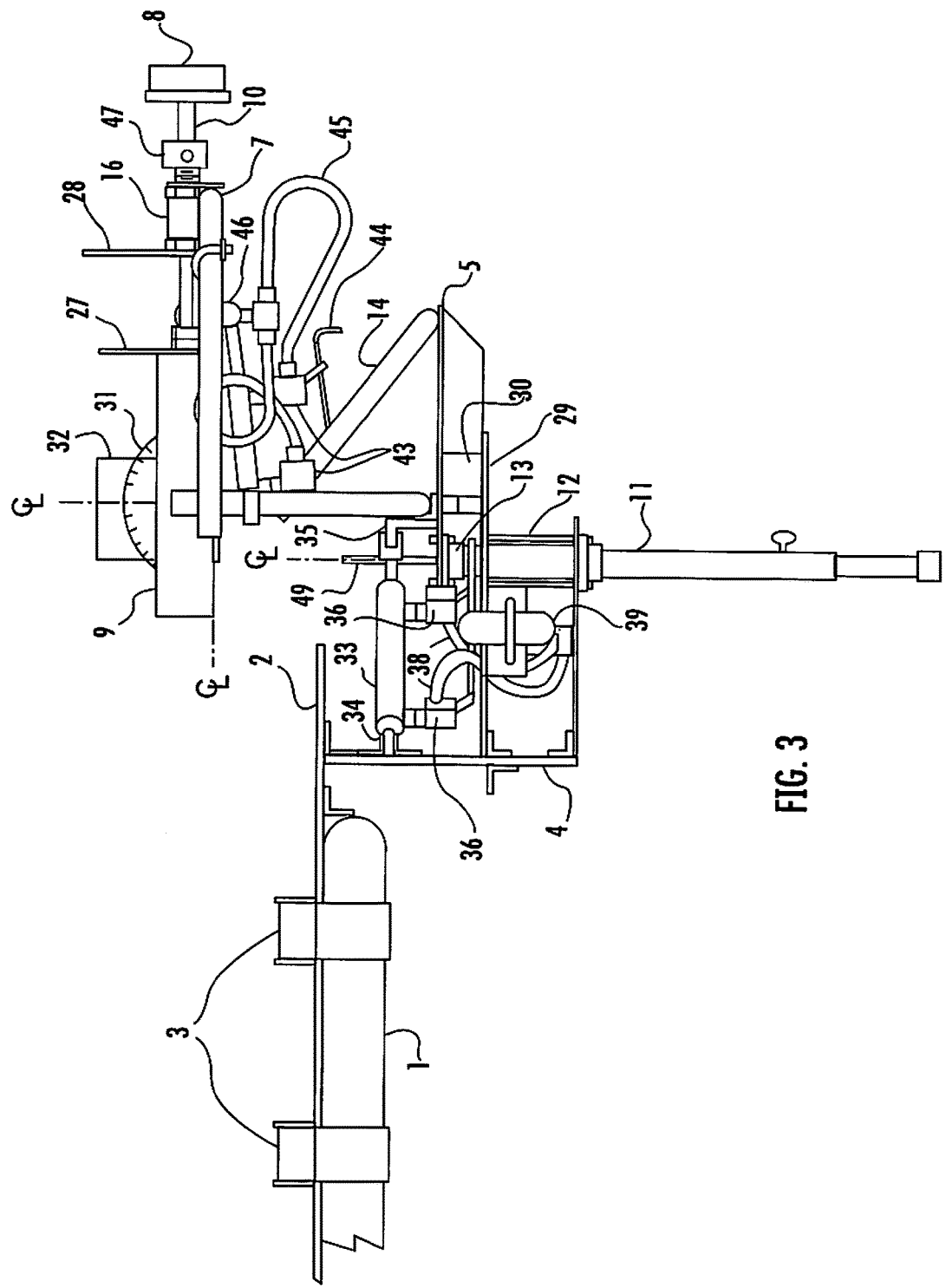
FIG. 3 is a left side elevation view of the device of FIG. 1.
Figure 4:
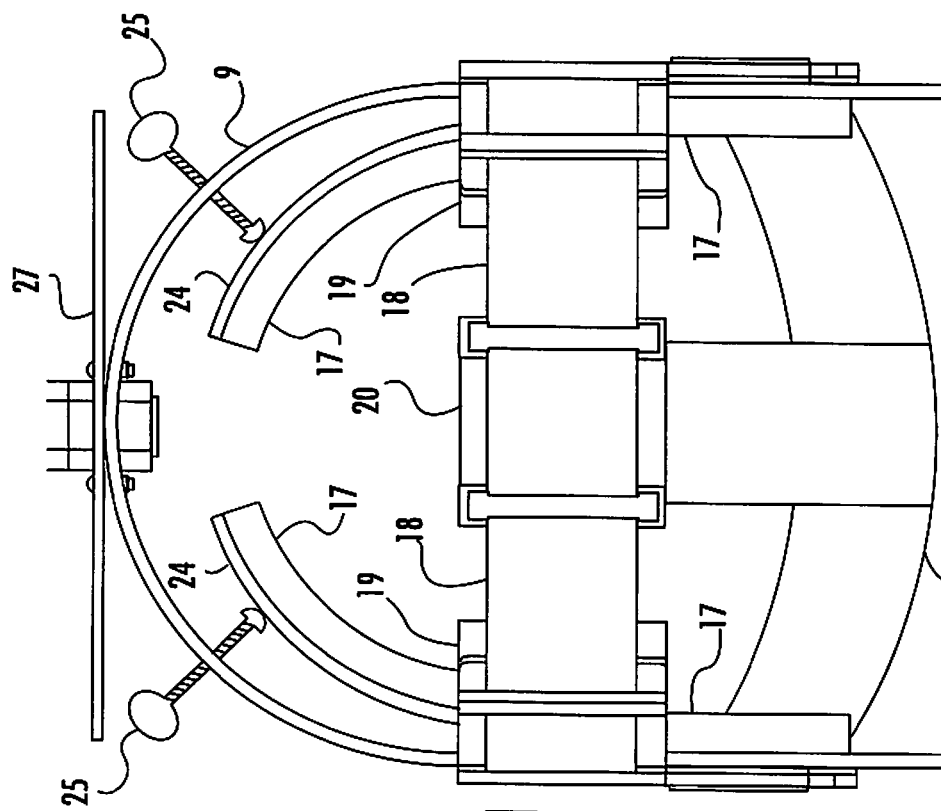
FIG. 4 is a front elevation view of a head harness of FIG. 1.
Figure 5:
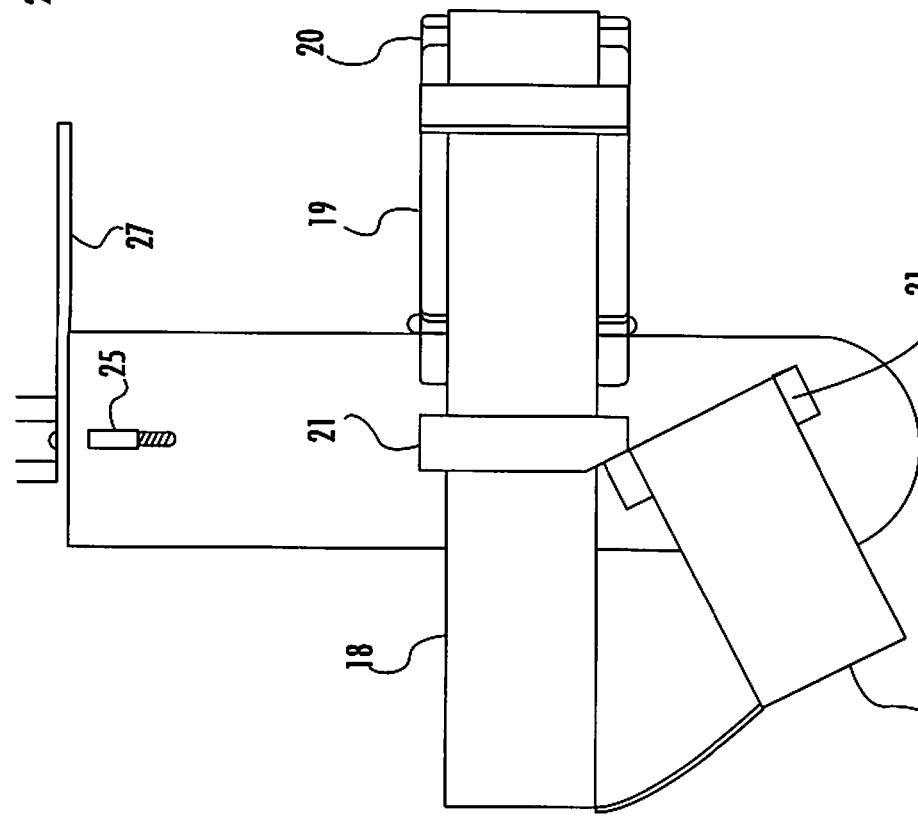
FIG. 5 is a right side elevation view of the head harness of FIG. 4.

FIGS. 1, 2, and 3 illustrate the overall view of the device incorporated into the PNF system of this invention. The device is attached to a treatment table (1) by placing the table board (2) on top of the treatment table (1) and securing it with two ratchet straps (3). The device also can be mounted on a wheeled trolley and attached to the end of the treatment table (1). The patient lies on the table board (2) with the head beyond the end of the table board (2). The weight of the patient stabilizes the table board (2) on the treatment table (1).

Now noting FIGS. 2 and 3, a stationary member (4) is secured to the bottom of the table board (2) and is supported from the floor by an adjustable support (11). The adjustable support (11) is a pipe and tube telescope locked by a thumb screw when the stationary member (4) is level and parallel to the floor. The adjustable support (11) is below and concentric with a shaft and bearing assembly (12) for a movable member (5), allowing it to support the weight of the device. The shaft and bearing assembly (12) allows the movable member (5) to turn in the horizontal plane on its shaft in the bearing which is part of the stationary member (4). The shaft is attached to a shaft bracket (13) mounted on the movable member (5). The centerline of the shaft and bearing assembly (12) corresponds with the patient's neck vertebra C7 which is the approximate bending point of the neck about the anteroposterior neck movement axis. The movable member (5) can turn approximately 45 degrees in either direction before an associated yoke (6) is stopped by the table board (2).

The yoke (6) is mounted on the movable member (5), and is stabilized by the yoke support (14). Each end of a handle (7) is attached to an upper end of the yoke (6) by a shoulder screw (15) shaft allowing the handle (7) to rotate up or down in the vertical plane about the mediolateral neck movement axis. The handle (7) is used to move the movable member (5) right or left and up or down. In the center of the handle (7) is mounted a head harness bearing (16) through which a head harness shaft (10) moves not only in a rotating motion about the craniocaudal neck movement axis, but also in and out along that axis. The internal end of the head harness shaft (10) is bolted to the head harness (9). On the external end of the head harness shaft (10) is a knob (8) which the therapist may move in or out to adjust for the head length and to rotate the head. The knob (8) can also be used to move the movable member (5) right or left and up or down. By way of example, the handle (7) can rotate approximately 45 degrees up and approximately 36 degrees down.

FIGS. 4, 5, 6 and 7 illustrate views of the head harness portion of the PNF stretching unit. The head harness member is composed of the head harness (9) which is U shaped flat aluminum bar. The top of the U is at the top of the head while the legs of the head harness (9) come down over the patient's ears. Sponge rubber pads (17) are attached to the inside of the head harness (9) with a hook and loop fastener so that varying head widths can be accommodated by changing the thickness of the sponge rubber pads (17). Sponge rubber is dense or firm so that head will not have relative motion with respect to head harness (9) movement when the head is secured within the head harness (9) by the head strap (18). A flap pad (19) is hinged to the front of the head harness (9) to allow for heads of different circumference. The flap pad (19) is a flat aluminum bar with a sponge rubber pad attached by a hook and loop fastener. The forehead pad (20) is reinforced strap with D rings on each side and a sponge rubber pad attached by hook and loop fasteners On the outside of the head harness (9) and each flap pad (19) are guide loops (21) to maintain the position of the head strap (18) when it is pulled tight. The head strap (18) is threaded through each guide loop (21) and is secured by one guide loop (21) to prevent it slipping out of the head harness (9). With the two ends of the head strap (18) at the front, one end is threaded through a D ring on the forehead pad (20) and turned back against itself. The other end of the head strap (18) is threaded through the other D ring and turned back against itself. Then the ends of the head strap (18) are pulled away from each other tightening the head strap (18) around the head. Each end of the head strap (18) is then brought against itself where hooks (22) on the ends are meshed with loops (23) on the internal strap locking the head strap (18) securely around the head. By pulling the head strap (18) ends away from each other the forces against the head are balanced. Top pads (24) are hinged inside the head harness (9) to allow for heads of different length so that the ears are comfortable against the sponge rubber pad (17). Thumb screws (25) are used to adjust the location of the top pad (24). An adjustable neck strap (26) is attached to the head harness (9) by guide loops (21) and helps secure the head within the head harness (9).

Referring to FIG. 1 through 7, an angular rotational gauge (27), such as a protractor is attached to the top of the head harness (9). An angular rotational indicator window (28) made of clear hard plastic and with an inscribed line is attached to the head harness bearing (16). By viewing the degree markings on the angular rotational gauge (27) through the angular rotational indicator window (28) and aligning its inscribed line with a degree marking on the angular rotational gauge (27), the angular rotation of the head can be determined. In an alternate embodiment, rotational angular displacement is measured by a linear potentiometer and recorded on a data processing system.

A horizontal angular gauge (29) inscribed with degree marks is attached to the stationary member (4). Mounted on the underneath side of the movable member (5) is horizontal angular indicator (30) which points to the degree marks on the horizontal angular gauge (29) indicating the angular horizontal movement of the movable member (5). In an alternate embodiment, horizontal angular displacement is measured by a linear potentiometer and recorded on a data processing system.

A vertical angular gauge (31), or protractor, is attached to the yoke (6) so that the center of the protractor is centered at the shoulder screw (15). A vertical angular indicator window (32) made of clear hard plastic and is attached to the handle (7) so that an inscribed line is perpendicular to the handle (7) and passes through the center of the shoulder screw (15). By viewing the degree markings on the vertical angular gauge (31) through the vertical angular indicator window (32) and aligning its inscribed line with a degree marking on the vertical angular gauge (31), the angular vertical movement of the handle (7) can be determined. In an alternate embodiment, vertical angular displacement is measured by a linear potentiometer and recorded on a data processing system.

Referring to FIGS. 2 and 3, the horizontal hydraulic cylinder (33) is used to lock the movable member (5) in place. The base of the cylinder is pinned in the cylinder pivot bracket (34) which is fixed on the stationary member (4). The cylinder piston rod clevis is pinned to the piston rod bracket (35) mounted on the movable member (5). The horizontal hydraulic cylinder (33) is a double acting cylinder which allows control of hydraulic fluid in both chambers of the cylinder. The two way toggle valves (36) at each port of the horizontal hydraulic cylinder (33) are connected together by a switch rod (37) attached to each toggle lever so that the two way toggle valves (36) are synchronized to be either open or closed. When both two way toggle valves (36) are open, the hydraulic fluid flows through the tubing (38) from one chamber to the other chamber. Because the chambers are different volumes, excess hydraulic fluid can move into the hydraulic oil reservoir (39) or in the case where additional hydraulic fluid is required, hydraulic fluid can be added to the flow from a first hydraulic oil reservoir (39). When both two way toggle valves (36) are closed, the incompressible hydraulic fluid is sealed in both chambers of the cylinder locking the piston in place.

The handle hydraulic cylinder (40) is used to lock the handle (7) in place. The base of the cylinder is pinned in a cylinder pivot bracket (41) which is fixed on the yoke (6). The cylinder piston rod clevis is pinned to piston rod bracket (42) mounted on the handle (7). The handle hydraulic cylinder (40) is also a double acting cylinder which allows control of hydraulic fluid in both chambers of the cylinder. The two way toggle valves (43) at each port of the handle hydraulic cylinder (40) are connected together by a switch rod (44) attached to each toggle lever so that the two way toggle valves (43) are synchronized to be either open or closed. When both two way toggle valves (43) are open, the hydraulic fluid flows through the tubing (45) from one chamber to the other chamber. Because the chambers are different volumes, excess hydraulic fluid can move into a second hydraulic oil reservoir (46) or in the case where additional hydraulic fluid is required, hydraulic fluid can be added to the flow from the hydraulic oil reservoir (46). When both two way toggle valves (43) are closed, the incompressible hydraulic fluid is sealed in both chambers of the cylinder locking the piston in place.

Figure 8:
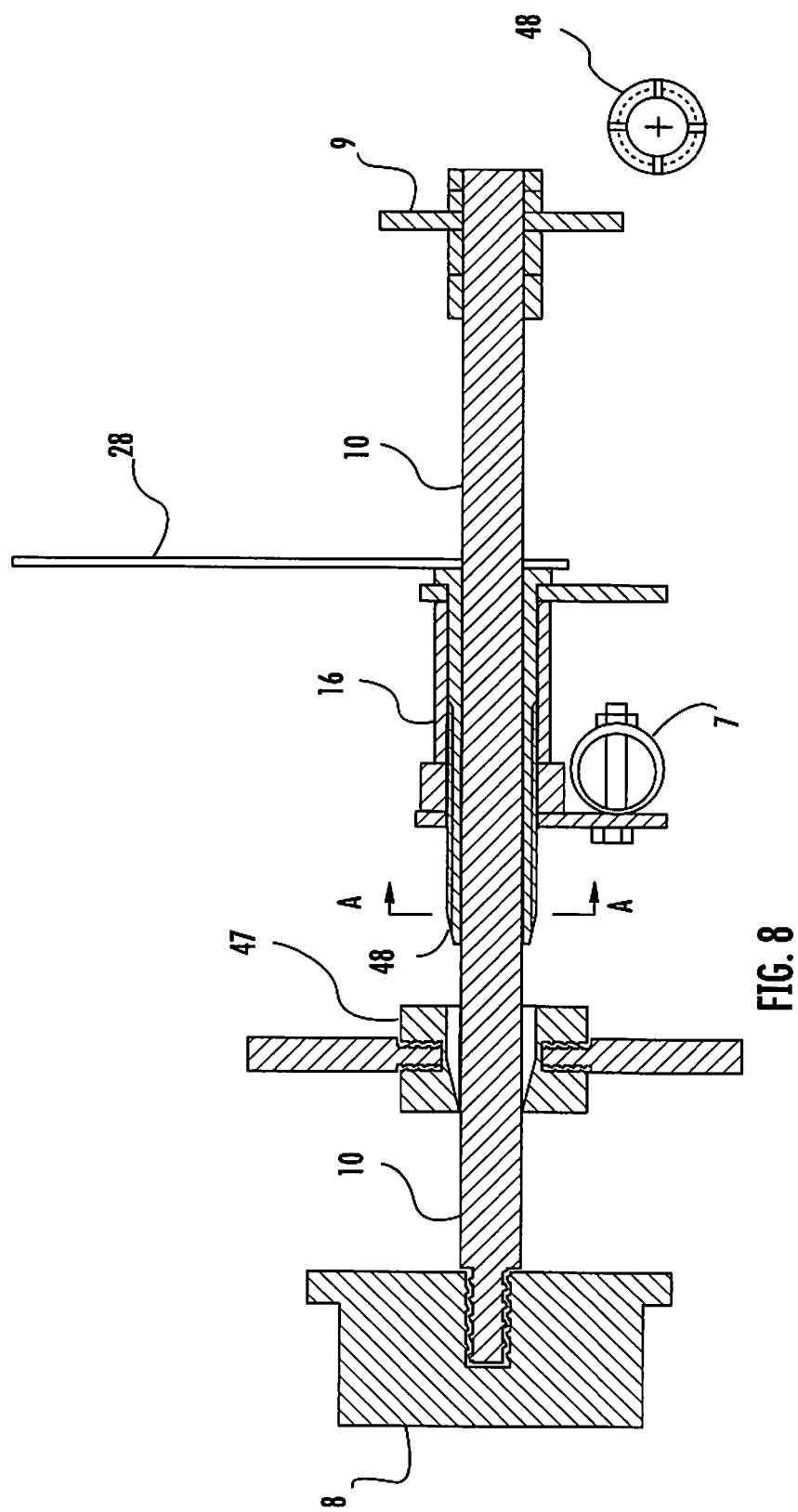
FIG. 8 is a cross-section of a head harness shaft and compression collet of FIG. 1.

Referring to FIG. 8, the head harness (9) is secured to the head harness shaft (10) with lock nuts and is locked into position when an associated collet nut (47) is screwed tightly onto a threaded collet (48) compressing the collet (48) onto the head harness shaft (10). The end of the collet (48) is split into four or more segments to allow for its compression (Cross Section A, FIG. 8). The collet (48) is a fixed part of the head harness bearing (16). Head harness bearing (16) is fixed to the handle (7) with bolts. The rotation of the head harness (9) is controlled by the knob (8) at the other end of the head harness shaft (10). No mechanical stop limits the rotation of the head harness shaft (10).

Methods of Use

The height of the treatment table (1) is adjusted to fit a seated therapist and the adjustable support (11) is extended and locked to the approximate length necessary to hold the stationary member (4) at the height of the treatment table (1). The table board (2) is placed on the treatment table (1) and the two ratchet straps (3) go around the table board (2) and the treatment table (1). The ratchet straps (3) are pulled tight securing the table board (2) to the treatment table (1). The adjustable support (11) is adjusted so that the bottom surface of the stationary member (4) is parallel to the floor and the thumb screw is tightened. The two way toggle valves (36) are opened by pulling the switch rod (37) and the movable member (5) is turned to the "zero" position on the horizontal angular gauge (29) indicated by the horizontal angular indicator (30). The two way toggle valves (36) are closed by pushing the switch rod (37) which then locks the movable member (5) in the "zero" position. The two way toggle valves (43) are opened by pulling the switch rod (44) and the handle (7) is turned to the "zero" position on the vertical angular gauge (31) indicated by inscribed line on the vertical angular indicator window (32). The two way toggle valves (43) are closed by pushing the switch rod (44) which then locks the handle (7) in the "zero" position. The collet nut (47) is turned counter-clockwise releasing the collet's (48) grip on the head harness shaft (10). The knob (8) is used to pull the head harness shaft (10) as far out as possible and turn it to "zero" on the angular rotational gauge (27) indicated by inscribed line on the angular rotational indicator window (28). The head can now be placed in the loose head harness (9).

The patient lies on his or her back on the table board (2) and treatment table (1) with the head extended beyond the table board (2) and into the head harness (9). The neck is positioned so that vertebra C7 is located over the pivot point indicator (49). The knob (8) on the head harness shaft (10) is moved toward the head if necessary. The head harness (9) may need adjustment to accept the head width by replacing the side pads (17) with either thicker or thinner pads. Adjustment for head length is made by moving the top pad (24) with the thumb screws (25) so that the ears are comfortable against the sponge rubber pad (17). The knob (8) on the head harness shaft (10) is moved for a final adjustment and "zeroed." The collet nut (47) is turned clockwise tightly squeezing the collet's (48) grip on the head harness shaft (10) and locking the head harness (9) in final position. The forehead pad (20) is placed in the middle of the forehead with the bottom touching the patient's eye brows. The neck strap (26) may need adjustment to support the neck by loosening the strap and securing the hooks into the loops which are sewn onto the neck strap (26). When the patient's head is comfortably in the head harness (9), the ends of the head strap (18) are threaded through the D rings on the forehead pad (20). The ends of the head strap (18) are pulled away from each other tightening the head strap (18) around the head. Each end of the head strap (18) is then brought against itself where hooks (22) on the ends are meshed with loops (23) on the internal strap locking the head strap (18) securely around the head. By pulling the head strap (18) ends away from each other the forces against the patient's head are balanced.

The therapist is now ready to start the PNF stretching procedures. With the seated therapist facing the patient's head and the knob in hand, the movable member (5) is unlocked by pulling the switch rod (37) and opening the two way toggle valves (36). The movable member (5) can now be moved right or left using either the handle (7) or the knob (8). For vertical movement, the handle (7) is unlocked by pulling the switch rod (44) and opening the two way toggle valves (43). The handle (7) can now be moved up or down using either the handle (7) or the knob (8). The head can now be moved in all directions by using either the handle (7) or the knob (8). Using the handle (7) or knob (8), the therapist passively stretches the muscle group to the end of its current range of motion. When the end point is reached, both switch rods (37 and 44) are pushed to close the two way toggle valves (36 and 43) and lock the head in its initial position. If it is desired to rotate the head, the collet nut (47) is turned counter clockwise releasing the grip of collet (48) on the head harness shaft (10) and the knob (8) is used to turn the head harness shaft (10) in either direction. The rotated head may then be locked in position by turning the collet nut (47)

clockwise until the head harness shaft (10) is immovable. The head is now locked in the initial end of range of motion position.

A record is then made on the patient's chart of the three initial angular displacements. The horizontal angular displacement is read by looking down where the horizontal angular indicator (30) shows the degrees moved from the center line on the horizontal angular gauge (29). The rotational angular displacement is read by looking through the angular rotational indicator window (28) and aligning the inscribed line with the degree marked on the angular rotational gauge (27). By moving to the right side of the movable member (5), the therapist can look through the vertical angular indicator window (32) and align the inscribed line with the degree marked on the vertical angular gauge (31). In an alternative embodiment, the angular displacements are measured by linear potentiometers and are recorded on a data processing system. For example, the linear potentiometers could be integrated with the hydraulic cylinders.

The patient then contracts the muscle group isometrically in the stretched position against resistance of the head harness for a brief period of time as directed by the therapist. The muscle group is then allowed to relax before being passively stretched again by the therapist to an increased range of motion, following which the muscles are again contracted isometrically in the stretched position against resistance by the head harness (9). This routine continues until no further range of motion is achieved or the patient becomes fatigued. In an alternative embodiment, the force applied by the patient is measured by four load cells (50) and recorded in a data processing system. Load cells are mounted to measure forces applied by the forehead, back of head and on each side of the head.

The therapist then records the end point of the range of motion on the patient's chart as the three final angular displacements. The horizontal angular displacement is read by looking down where the horizontal angular indicator (30) shows the degrees moved from the center line on the horizontal angular gauge (29). The rotational angular displacement is read by looking through the angular rotational indicator window (28) and aligning the inscribed line with the degree marked on the angular rotational gauge (27). When the therapist moves to the right side of the movable member (5), he or she can look through the vertical angular indicator window (32) and align the inscribed line with the degree marked on the vertical angular gauge (31). In an alternative embodiment, the angular displacements are measured by linear potentiometers and are recorded on a data processing system.

This sequence is continued for the head placed at different angles as the therapist deems necessary. After the PNF stretching therapy is completed with improved range of motion, the device can be unlocked in one plane while the other two planes remain locked and the patient can exercise the joint through the improved range of motion. Then the initially unlocked plane can be locked and one of the other planes can be unlocked so that the patient can undergo PNF stretching of the neck in the second plane. The same can be done for PNF stretching in the third plane.

An alternative use of this device is as a therapeutic device for holding the head in a secure fixed position while the therapist applies therapy to the neck with both hands or with one hand while resting the other. The exact position of the head can be recorded using the angular measuring means.

As a second alternative use is as a diagnostic device for measuring the range of motion of the neck and head and for measuring the applied forces of the head against the resistance of the device. These measurements would be taken before treatment as a baseline and as treatment progresses to determine improvement.

The neck is a very complex biological mechanism, having multiple joints with complex interactions. Generally speaking, however, the neck can be understood to allow rotational movement about three axes: the anteroposterior (front-to-back) axis; the mediolateral (side-to-side) axis, and the craniocaudal (top-to-bottom). Similarly, the anteroposterior and mediolateral axes can be considered to define a transverse plane, the anteroposterior and craniocadual axes can be considered to define a sagittal plane (i.e., the midsagittal plane), and the mediolateral and craniocaudal axes can be considered to define a coronal plane. The device is preferably configured such that anteroposterior and craniocaudal axes can intersect at the cervical vertebra C7. The mediolateral and craniocaudal axes preferably also intersect, though not necessarily at C7.

Benefits afforded by the present invention can include:
1. Improvement of passive joint range of motion of the neck using the PNF technique by applying mechanical resistance to forces exerted by the patient at the target joint.
2. Improvement of active joint range of motion by allowing the patient to freely exercise the neck in one plane of motion while other planes of motion are held in a locked position.
3. Reduction in muscular hypertonicity or spasms in the neck by using mechanical resistance to force exerted by the patient.
4. Facilitated measurement of improved range of motion of the neck.
5. Facilitated locking in each plane of motion by the use of a unique hydraulic lock or a mechanical collet lock.

It will be appreciated by those skilled in the art that many modifications and embodiments of the above-described invention will come to the mind of one skilled in the art having the benefit of the teachings presented in the foregoing description and the associated drawings. Therefore, it is to be understood that the invention is not to be limited to the specific embodiment disclosed herein, and that modifications and alternate embodiments are intended to be included within the scope of this invention.

What is claimed is:

1. A neck movement support device comprising:
a stationary member;
a movable member connected to the stationary member at a first pivot point, the movable member being rotatable relative to the stationary member about the first pivot point, the first pivot point defining an anteroposterior neck movement axis;
a yoke extending away from the movable member and rotatable therewith about the anteroposterior neck movement axis;
a handle connected to the yoke at a second pivot point, the handle being rotatable relative to the yoke about the second pivot point, the second pivot point defining a mediolateral neck movement axis;
a head harness connected to the handle at a third pivot point, the head harness being rotatable relative to the handle about the third pivot point, the third pivot point defining a craniocaudal neck movement axis; and
a table board connected to the stationary member and configured to removably overlie an upper surface of a patient treatment table, such that the table board, stationary member, movable member, yoke, handle and head harness are removable from the patient treatment table as a unit, remaining connected with one another via the first, second and third pivot points;

wherein the first, second and third pivot points are located such that the craniocaudal neck movement axis intersects both the mediolateral neck movement axis and the anteroposterior neck movement axis; and wherein a head of a user is securable to the head harness in a supine position, so as to constrain the head to move or remain stationary along with the head harness about the anteroposterior, mediolateral and craniocaudal neck movement axes, the device being configured such that, with the head of the user secured in the harness in the supine position, the anteroposterior and craniocaudal neck movement axes are constrained to intersect at cervical vertebra C7 of the user.

2. The device of claim 1, further comprising a movable member shaft and bearing assembly supporting the movable member on the stationary member for rotary motion relative thereto about the anteroposterior neck movement axis.

3. The device of claim 1, further comprising at least one shoulder screw rotatably connecting the handle to the yoke about the mediolateral neck movement axis.

4. The device of claim 3, wherein the at least one shoulder screw includes a pair of shoulder screws rotatably connecting opposite sides of the handle to respective opposite sides of the yoke.

5. The device of claim 1, wherein rotary motion of the handle relative the yoke about the mediolateral neck axis is limited in the anterior and posterior directions.

6. The device of claim 5, wherein anterior and posterior limits are 45 and 36 degrees, respectively.

7. The device of claim 1, further comprising a head harness shaft and bearing supporting the head harness on the handle for rotary motion relative thereto about the craniocaudal neck movement axis.

8. The device of claim 7, wherein the head harness shaft also supports the head harness on the handle for translational movement along the craniocaudal neck movement axis.

9. The device of claim 7, further comprising a knob arranged on an end of the head harness shaft opposite the head harness.

10. The device of claim 1, further comprising at least one strap for securing the table board to the patient treatment table.

11. The device of claim 1, wherein interference between the table board and the yoke effects lateral limits to rotary motion of the movable member about the anteroposterior neck movement axis.

12. The device of claim 11, wherein the lateral limits are +/−45 degrees.

13. The device of claim 1, further comprising a support leg connected to a side of the stationary member opposite the movable member.

14. The device of claim 13, wherein the support leg is coaxial with the anteroposterior neck movement axis.

15. The device of claim 13, wherein a length of the support leg is adjustable in the anteroposterior neck movement axis.

16. The device of claim 1, wherein the head harness includes a padded U shaped bar.

17. The device of claim 16, wherein the head harness further includes at least one head strap attached to the padded U shaped bar and operable to fasten the head about the craniocaudal neck movement axis.

18. The device of claim 17, wherein the head harness further includes at least one flap pad hinged to the padded U shaped bar and engaged by the head strap.

19. The device of claim 17, wherein the head harness further includes at least one forehead pad mounted on the head strap.

20. The device of claim 17, wherein the head harness further includes a neck strap connected to the U shaped bar.

21. The device of claim 16, wherein the head harness further includes a pair of opposing top pads hinged inside the U shaped bar.

22. The device of claim 21, wherein the head harness further includes a pair of thumbscrews extending through the U shaped bar and operable to adjust the top pads.

23. The device of claim 16, wherein the head harness further includes a plurality of load cells configured to measure forces applied by the head.

24. The device of claim 1, further comprising at least one rotation measurement mechanism operable to determine relative rotary motion between at least one of:
the movable member and the stationary member;
the handle and the yoke; and
the head hardness and the handle.

25. The device of claim 24, wherein the at least one rotation measurement mechanism includes a mechanical indicator.

26. The device of claim 24, wherein the at least one rotation measurement mechanism includes a linear potentiometer.

27. The device of claim 24, wherein the at least one rotational measurement mechanism includes three rotation measurement mechanisms operable to determine relative rotary motion between the movable member and the stationary member, the handle and the yoke and the head hardness and the handle, respectively.

28. The device of claim 1, further comprising at least one locking mechanism operable to fix relative rotary motion between at least one of:
the movable member relative to the stationary member;
the handle relative to the yoke; and
the head harness relative to the handle.

29. The device of claim 28, wherein the at least one locking mechanism includes a hydraulic cylinder.

30. The device of claim 28, wherein the at least one locking mechanism includes a collet nut threaded onto a collet.

31. A method of using the neck movement support device of claim 1 in proprioceptive neuromuscular facilitation (PNF) therapy, the method comprising:
securing the head of the user in the head harness with the user in the supine position; and
moving the head harness to move a neck of the user about at least one of the anteroposterior, mediolateral and craniocaudal neck movement axes.

32. The method of claim 31, further comprising at least one of:
holding the head in a fixed position during neck therapy;
measuring a range of motion of the head and neck; and
measuring applied forces of the head against the head harness.

* * * * *